(12) United States Patent  (10) Patent No.: US 7,806,883 B2
Fossum et al.  (45) Date of Patent: Oct. 5, 2010

(54) ABSORBENT ARTICLES HAVING A BREATHABLE STRETCH LAMINATE

(75) Inventors: Renae Dianna Fossum, Middletown, OH (US); Arman Ashraf, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 523 days.

(21) Appl. No.: 11/333,135

(22) Filed: Jan. 17, 2006

(65) Prior Publication Data

US 2007/0167929 A1    Jul. 19, 2007

(51) Int. Cl.
*A61F 13/15* (2006.01)
(52) U.S. Cl. .................. 604/385.22; 604/385.24; 604/385.27; 604/366; 604/370; 604/367
(58) Field of Classification Search ............ 604/385.22, 604/385.24, 385.27, 366, 370, 367
See application file for complete search history.

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 4,525,407 A * | 6/1985 | Ness | 428/138 |
| 4,610,678 A | 9/1986 | Weisman et al. | |
| 4,662,875 A | 5/1987 | Hirotsu et al. | |
| 4,673,402 A | 6/1987 | Weisman et al. | |
| 4,695,278 A | 9/1987 | Lawson | |
| 4,699,622 A | 10/1987 | Toussant et al. | |
| 4,795,454 A | 1/1989 | Dragoo | |
| 4,808,178 A | 2/1989 | Aziz et al. | |
| 4,834,735 A | 5/1989 | Alemany et al. | |
| 4,846,815 A | 7/1989 | Scripps | |
| 4,888,231 A | 12/1989 | Angstadt | |
| 4,892,536 A | 1/1990 | Desmarais et al. | |
| 4,894,060 A | 1/1990 | Nestegard | |
| 4,909,803 A | 3/1990 | Aziz et al. | |
| 4,940,464 A | 7/1990 | Van Gompel et al. | |
| 4,946,527 A | 8/1990 | Battrell | |
| 4,963,140 A | 10/1990 | Robertson et al. | |
| 4,965,122 A | 10/1990 | Morman | |
| 4,981,747 A | 1/1991 | Morman | |
| 4,990,147 A | 2/1991 | Freeland | |

(Continued)

FOREIGN PATENT DOCUMENTS

EP    0 963 760 A    12/1999

(Continued)

OTHER PUBLICATIONS

PCT Search Report, mailed Jan. 16, 2007, 4 pages.

*Primary Examiner*—Jacqueline F. Stephens
(74) *Attorney, Agent, or Firm*—Eric T. Addington; Thibault Fayette

(57) ABSTRACT

An absorbent article may comprise a topsheet; a backsheet joined with the topsheet; an absorbent core between the topsheet and backsheet; and an elastic element comprising a breathable stretch laminate. The breathable stretch laminate may comprise a first substrate; and an elastic member joined to the first substrate, wherein said elastic member comprises a polyurethane. The breathable stretch laminate may exhibit a MVTR greater than about 300 grams per square meter per 24 hours and a force relaxation of less than about 50% after about 10 hours at 100° F. and 50% elongation.

11 Claims, 5 Drawing Sheets

U.S. PATENT DOCUMENTS

| | | | |
|---|---|---|---|
| 5,037,416 A | 8/1991 | Allen et al. | |
| 5,092,861 A | 3/1992 | Nomura et al. | |
| 5,114,781 A | 5/1992 | Morman | |
| 5,116,662 A | 5/1992 | Morman | |
| 5,137,537 A | 8/1992 | Herron et al. | |
| 5,147,345 A | 9/1992 | Young et al. | |
| 5,151,092 A | 9/1992 | Buell et al. | |
| 5,156,793 A | 10/1992 | Buell et al. | |
| 5,167,897 A * | 12/1992 | Weber et al. | 264/288.8 |
| 5,221,274 A | 6/1993 | Buell et al. | |
| 5,226,992 A | 7/1993 | Morman | |
| 5,242,436 A | 9/1993 | Weil et al. | |
| 5,246,433 A | 9/1993 | Hasse et al. | |
| 5,260,345 A | 11/1993 | Desmarais et al. | |
| 5,269,775 A | 12/1993 | Freeland et al. | |
| 5,336,545 A | 8/1994 | Morman | |
| 5,342,338 A | 8/1994 | Roe | |
| 5,387,207 A | 2/1995 | Dyer et al. | |
| 5,397,316 A | 3/1995 | Lavon et al. | |
| 5,499,978 A | 3/1996 | Buell et al. | |
| 5,507,736 A | 4/1996 | Clear et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,591,152 A | 1/1997 | Buell et al. | |
| 5,607,760 A | 3/1997 | Roe | |
| 5,609,587 A | 3/1997 | Roe | |
| 5,625,222 A | 4/1997 | Yoneda et al. | |
| 5,635,191 A | 6/1997 | Roe et al. | |
| 5,643,588 A | 7/1997 | Roe et al. | |
| 5,865,823 A | 2/1999 | Curro | |
| 5,897,545 A | 4/1999 | Kline et al. | |
| 5,957,908 A | 9/1999 | Kline et al. | |
| 6,004,306 A | 12/1999 | Robles et al. | |
| 6,107,537 A | 8/2000 | Elder et al. | |
| 6,120,487 A | 9/2000 | Ashton | |
| 6,120,489 A | 9/2000 | Johnson et al. | |
| H2011 H * | 1/2002 | Freiburger et al. | 604/381 |
| 6,432,098 B1 | 8/2002 | Kline et al. | |
| 6,590,136 B1 | 7/2003 | Young et al. | |
| 6,843,134 B2 | 1/2005 | Anderson et al. | |
| 6,932,800 B2 | 8/2005 | Lavon et al. | |
| 2002/0019187 A1 | 2/2002 | Carroll | |
| 2002/0119300 A1 | 8/2002 | Taylor | |
| 2003/0088228 A1 | 5/2003 | Desai et al. | |
| 2003/0091807 A1 | 5/2003 | Desai et al. | |
| 2003/0199844 A1 | 10/2003 | Lavon et al. | |
| 2003/0207640 A1 * | 11/2003 | Anderson et al. | 442/394 |
| 2003/0233082 A1 | 12/2003 | Kline et al. | |
| 2004/0013852 A1 | 1/2004 | Curro et al. | |
| 2004/0024379 A1 | 2/2004 | Lavon et al. | |
| 2004/0030314 A1 | 2/2004 | Lavon et al. | |
| 2004/0039361 A1 | 2/2004 | Lavon et al. | |
| 2004/0167486 A1 | 8/2004 | Busam et al. | |
| 2004/0222553 A1 | 11/2004 | Desai et al. | |
| 2005/0228356 A1 | 10/2005 | Lavon et al. | |

FOREIGN PATENT DOCUMENTS

| | | |
|---|---|---|
| WO | WO 98/29241 A | 7/1998 |
| WO | WO 01/10373 A | 2/2001 |
| WO | WO 01/36726 A | 5/2001 |
| WO | WO 02/34511 A | 5/2002 |
| WO | WO 02/051938 A2 | 7/2002 |

* cited by examiner

ABSORBENT ARTICLES HAVING A BREATHABLE STRETCH LAMINATE

FIELD OF THE INVENTION

This invention is directed to absorbent articles such as diapers, training pants, adult incontinence articles, feminine hygiene articles, and the like comprising a breathable stretch laminate.

BACKGROUND OF THE INVENTION

It has long been known in the field of disposable absorbent articles that it is desirable to construct absorptive devices, such as disposable diapers with fasteners, pull-on diapers, training pants, sanitary napkins, pantiliners, incontinence briefs, and the like, with stretch laminates to improve the ease of motion and maintenance of a sustained fit. Stretch laminates allow the disposable absorbent article to accommodate a range of different sized wearers. A disposable absorbent article may have stretch laminates in a number of its structures including the waist band, leg cuffs, side panels, elasticized topsheets, backsheet, ears, and fastening system.

Various vapor permeable, liquid impermeable polymeric films are known in the art. For example, one method of making a polymeric film vapor permeable, involves mixing a matrix polymer with a quantity (e.g., 10-70% by weight) of an organic or inorganic particulate filler such as, for example, calcium carbonate, and extruding a film from the blend. The matrix polymer may include a polyolefin, such as polyethylene or polypropylene, or various olefin copolymers. The film may be a monolayer film, a multilayer film which contains the polymer/filler matrix as a primary layer along with thin breathable skin layers, or a multilayer film having more than one polymer/filler matrix layer. The film may be stretched. The particulate filler serves as nucleation sites causing the formation of voids in the film. However, films and laminates made from the films generally are not elastic. Even if an elastomer is used in lieu of the polyolefin, the relatively high concentration of particulate filler often degrades the elastic character and tensile properties of the resulting film.

Another common method for making a polymeric vapor permeable film involves aperturing the film during the formation process. For example, needle-punching is a well known process for aperturing films. Apertures may also be formed by subjecting the film to fluid pressure such as a water jet or air jet. While these methods may be used to make elastomeric films breathable, the resulting apertured elastomeric film may exhibit reduced tensile properties. In particular, apertured films often have reduced tensile strengths compared to equivalent non-apertured, monolithic films. In addition, apertured films are, in general, more susceptible to tear and tear propagation while being held at a constant strain when compared to non-apertured films.

Even when breathable elastomers and breathable stretch laminates are formed, these products may not exhibit mechanical characteristics ideally suited for use in disposable absorbent articles. One critical characteristic for stretch laminates for use in disposable absorbent articles such as disposable absorbent articles is that the stretch laminate should exhibit a low force relaxation.

Stretch laminates (particularly for use in disposable absorbent articles) ideally should exhibit high breathability with a minimal amount of force relaxation. Force relaxation quantifies an elastomer's loss of force as a result of a constant strain and hold at a predetermined strain, temperature, and time. Many diaper components comprise a stretch laminate. The elastic character of the component often improves the fit and function of the diaper. For example, elasticized side panels are common on disposable absorbent articles such as pant-type diapers. The elasticized side panels provide a snug, conforming fit that translates to improved containment of exudates. During wear, the elasticized side panels are maintained in an elongated state, and the elasticized side panel may exert an unload force. Over time, the unload force may diminish. If the elasticized side panel loses too much force, the diaper is prone to sagging which can result in increased leakage.

Another factor to be considered in stretch laminate construction is the hysteresis properties of the elastomeric material. The elastomeric material should not exhibit unnecessarily large hysteresis area under the curve since this evidences the presence of lower unload forces at lower strains (e.g., lower unload forces near strain exhibited in actual product use and application). Lower unload forces could indirectly effect the product fit. One approach to determine the improved properties of stretch laminate is by calculating the load (i.e., 200% strain) to unload (i.e., 50% return load strain). It is desirable to provide a stretch laminate with a low load to unload ratio.

Accordingly, it would be desirable to provide a disposable absorbent article comprising a stretch laminate that exhibits a requisite degree of breathability while maintaining a low degree of force relaxation. The breathable stretch laminate may exhibit a high degree of extensibility with a minimal degree of set. It would also be desirable to provide a method for making such a disposable absorbent article. It is also desirable to provide a disposable absorbent article comprising a breathable stretch laminate that exhibits a requisite degree of breathability and requiring low load forces while maintaining a low degree of force relaxation.

SUMMARY OF THE INVENTION

The present invention relates to an absorbent article having a topsheet; a backsheet joined with the topsheet; an absorbent core between the topsheet and backsheet; and an elastic element comprising a breathable stretch laminate. The breathable stretch laminate may comprise a first substrate; and an elastic member joined to the first substrate, wherein said elastic member comprises a polyurethane. The breathable stretch laminate may exhibit a MVTR greater than about 300 grams per square meter per 24 hours and a force relaxation of less than about 50% after about 10 hours at 100° F. and 50% elongation.

The present invention further relates to an absorbent article having a topsheet; a backsheet joined with the topsheet; an absorbent core between the topsheet and backsheet; and an elastic element comprising a breathable stretch laminate. The elastic element includes a breathable zero strain stretch laminate comprising an incrementally stretched first nonwoven; and an elastic member joined to the incrementally stretched first nonwoven. The elastic member comprises a phase-separating material having at least a first phase with a first glass transition temperature of less than −40° C. and a second phase with a second glass transition temperature of greater than 100° C., and wherein said phase-separating material comprises a polyurethane hard phase. The breathable zero strain stretch laminate exhibits a MVTR greater than about 300 grams per square meter per 24 hours, a force relaxation of less than about 50% after about 10 hours at 100° F. and 50% elongation, and a first cycle 200% load to 50% unload ratio of less than about 16.

The present invention further relates to methods by which to form the breathable stretch laminate.

DETAILED DESCRIPTION OF THE PRESENT INVENTIONS

Figure 1A:
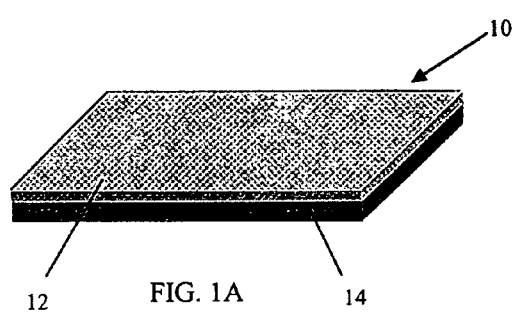
FIGS. 1A-D are perspective views of embodiments of the breathable stretch laminate.

The absorbent articles of the present invention comprise a breathable stretch laminate. The breathable stretch laminate may be used within the absorbent article wherever elastic properties are desired. The breathable stretch laminate generally comprises an elastic member joined to a substrate. The elastic member may be a polyurethane. The breathable stretch laminate exhibits a Moisture Vapor Transmission Rate (MVTR) of at least about 300 grams per square meter per 24 hours. In other embodiments, the breathable stretch laminate exhibits a MVTR of at least about 700 grams per square meter per 24 hours or of at least about 1100 grams per square meter per 24 hours. The breathable stretch laminate exhibits a force relaxation of less than about 50 percent after about 10 hours at 100° F. and 50% elongation I. Definitions As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on diapers, pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Proximal" and "Distal" refer respectively to the location of an element relatively near to or far from the longitudinal or lateral centerline of a structure (e.g., the proximal edge of a longitudinally extending element is located nearer to the longitudinal centerline than the distal edge of the same element is located relative to the same longitudinal centerline).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal"

"Lateral" refers to a direction running from a longitudinal edge to an opposing longitudinal edge of the article and generally at a right angle to the longitudinal direction. Directions within 45 degrees of the lateral direction are considered to be "lateral."

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Extendibility" and "extensible" mean that the width or length of the component in a relaxed state can be extended or increased.

"Elastic," "elastomer," and "elastomeric" refer to a material which generally is able to extend to a strain of at least 50% without breaking or rupturing, and is able to recover substantially to its original dimensions after the deforming force has been removed.

"Elastomeric material" is a material exhibiting elastic properties. Elastomeric materials may include elastomeric films, scrims, nonwovens, and other sheet-like structures.

"Outboard" and "inboard" refer respectively to the location of an element disposed relatively far from or near to the longitudinal centerline of the diaper with respect to a second element. For example, if element A is outboard of element B, then element A is further from the longitudinal centerline than is element B.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Stretch laminate" refers to an elastic member that is attached to at least one substrate such as a polymeric film, a nonwoven, a woven, or a scrim. The elastic member may be attached to the material by any of a number of bonding methods known to those skilled in the art, including adhesive bonding, thermal bonding, pressure bonding, ultrasonic bonding, and the like. A stretch laminate is generally able to extend to a strain of at least 50% without breaking or rupturing, and is able to recover substantially to its original dimensions after the deforming force has been removed.

"Substrate" refers to a sheet-like material. Suitable substrates include nonwoven webs, woven webs, knitted fabrics, films, film laminates, apertured films, nonwoven laminates, sponges, foams, scrims, and any combinations thereof. Suitable substrates may comprise natural materials, synthetic materials, or any combination thereof.

"Relaxed" or "relaxed state" means the state where no forces are applied to a structure or element (other than naturally occurring forces such as gravity).

"Copolymer" refers to a polymer synthesized from two or more monomers with different chemical structures.

"Breathable Monolithic Films" are non-porous, non-apertured films that allow moisture vapor to be transmitted through the film via diffusion, absorption, and/or convection. Films that have a moisture vapor transmission rate of about 300 g/m$^2$/24 hours or less are considered non-breathable.

II. Breathable Stretch Laminate

A. Structure

The breathable stretch laminate 10 (BSL) of the present invention comprises an elastic member 12 joined to a first substrate 14. Joining of the elastic member 12 and the substrate 14 may be conducted by a variety of bonding methods such as heat bonds, pressure bonds, ultrasonic bonds, mechanical bonds, adhesive bonds, or any other suitable attachment means or combinations of these attachment means as are known in the art. In certain embodiments, the elastic member 12 may exhibit sufficient tack adhere to the substrate 14. In other embodiments, the elastic member 12 may be applied to the substrate 14 in a molten or softened state such that the elastic member 12 fuses with or physically interlocks the substrate 14. The dimensions of the breathable stretch laminate 10 are generally limited only by the end-use of the breathable elastic laminate 10.

The elastic member 12 may comprise a variety of forms including, but are not limited to films, bands, strands, individualized fibers, scrims, cross-hatch arrays, foams, or combinations thereof. In a certain embodiments, the elastic member 12 is a monolithic film. A monolithic film is a non-porous, non-apertured film that can be prepared via typical film-forming methods such as solvent-casting or extrusion. Breathable monolithic films generally comprise a continuous hydrophilic moiety for rapid diffusion of water vapor through the film.

Figure 1B:
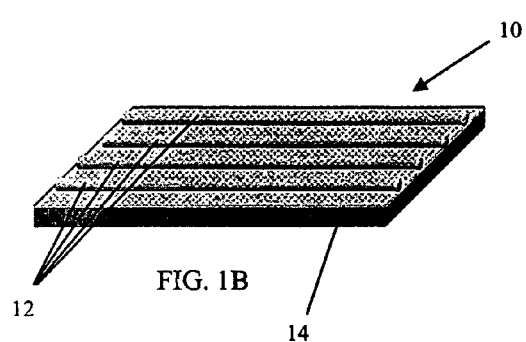
Figure 1C:
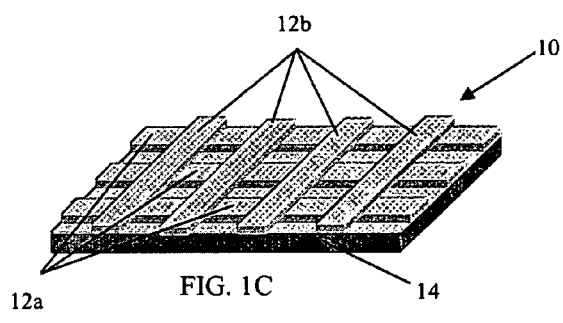

FIGS. 1A-D depict several suitable embodiments of the breathable stretch laminate 10. FIG. 1A depicts a breathable stretch laminate 10 having an elastic member 12 in the form of a monolithic film joined with a substrate 14. The elastic member 12 and the substrate 14 are shown as being coterminous; however, either layer may have dimensions differing from the other layer. FIG. 1B depicts a BSL 10 having one or more elastic members 12 joined with a substrate 14. The elastic members 12 may take the form a strand, yarn, ribbon, or the like. FIG. 1C depicts a BSL 10 having one or more elastic members in the form of a cross-hatch array joined with a substrate 14. A cross-hatch array may be formed in one instance by joining a plurality of elastic members 12a in parallel to the substrate 14. A second plurality of elastic members 12b may be joined in parallel to the substrate 14. The second plurality 12b may be joined in a non-parallel configuration to the first plurality 12a. A cross-hatch array may also be formed by hot needle punching or other perforation technique of an elastomeric film. A cross-hatch array may also be formed from a porous, macroscopically-expanded, three-dimensional elastomeric web as described in U.S. Patent Application Publication No. 2004/0013852. The publication describes how the cross-hatch array can be achieved by forming the film on a porous forming structure and applying a fluid pressure differential across the thickness of the film. The fluid pressure differential causes the film to conform to the supporting structure and rupture thereby creating a cross-hatch array.

Figure 1D:
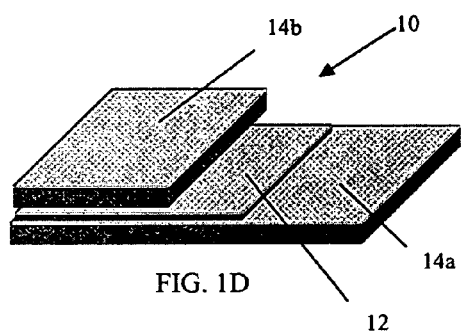

FIG. 1D depicts a breathable stretch laminate 10 having one or more elastic members 12 (FIG. 1D depicts the elastic member 12 as a film) joined to two or more substrates: first substrate 14a and second substrate 14b. The particular order of the breathable stretch 10 layers can vary; however, in the embodiment depicted, the elastic members 12 are disposed between the first substrate 14a and the second substrate 14b, and may be bonded to one or both. The first and second substrate 14a, 14b may comprise the same or different material.

B. Method of Making

The techniques for the formation of stretch laminates are well known in the art, and these techniques may be applicable in the formation of the BSL 10 of the present invention. One technique for creating a stretch laminate, which is commonly known as "stretch bonding," involves at least one elastic member 12 being joined to a substrate 14 while the elastic member 12 is in an elongated. The elastic member 12 may be in any well known form such as a strand, band, ribbon, film, scrim, or the like. Generally, the elastic member may be elongated to at least 25% of its relaxed length. An adhesive may be used to improve the attachment between the elastic member 12 and the substrate 14. After joining, the elastic member 12 is allowed to recovery thereby gathering the substrate and creating a stretch laminate.

Another technique for creating a stretch laminate, which is commonly known as "neck bonding," involves an elastic member 12 being bonded to a substrate 14 while the substrate is extended and necked. The resulting laminate is stretchable and generally exhibits elastic character in a direction generally parallel to the direction of necking of the substrate 14. In certain embodiments, the substrate 14 may be a non-elastic substrate. Examples of neck-bonded laminates are described in U.S. Pat. Nos. 5,226,992; 4,981,747; 4,965,122; and 5,336,545. A variant of "neck bonding" involves bonding an elongated elastic member 12 to a necked substrate 14. An adhesive may be used to improve the attachment between the elastic members and the substrate. Examples of such bonded laminates are described in U.S. Pat. Nos. 5,114,781 and 5,116,662.

In another technique for forming a stretch laminate, elastic members can be attached to a substrate in either a relaxed configuration or partially stretched configuration. An adhesive may be used to improve the attachment between the elastic members and the substrate. The resulting laminate can be made stretchable (or more stretchable in the case of partially stretched strands or film) by subjecting the laminate to an elongation process which elongates the substrate permanently, but elongates the elastic members only temporarily. Such processes are known in the art as "zero strain" stretch laminate formation. In certain embodiments, a zero strain stretch laminate may be subjected to incremental stretching. Incremental stretching may be performed by a pair of meshing corrugated rolls. The corrugated rolls support the laminate during the stretching operation at a plurality of closely spaced locations which correspond to the width of the corrugations. This results in a substantially uniform incremental stretching of each unsupported segment of the laminate between adjacent support points rather than highly localized stretching as often occurs when only the outermost extremities of the web are subjected to tension (e.g., laminate subjected to tensioning rolls or off-speed rolls). A suitable zero strain incremental stretching process is described in U.S. Pat. Nos. 5,167,897, 5,156,793, and 6,843,134.

An alternate technique for the formation of a stretch laminate is disclosed in U.S. Patent Application Publication Nos. 2003/0088228A1, 2003/0091807A1, and 2004/0222553A1.

The technique disclosed in these publications involves forming the elastic member by hot melt application of one or more elastomeric compositions onto a substrate to form one or more elastic members followed by the incremental stretching of the substrate so as to confer the stretch properties of the elastomer to the substrate. In certain embodiments, the elastic member may be formed by hot melt application of one or more thermoplastic elastomers onto an incrementally stretched substrate. Suitable application methods include, for example, direct gravure, offset gravure, and flexographic printing. Each of these methods allows deposition of an amount of elastomer in any shape and direction, thus providing substantial flexibility in the stretch character exhibited by the stretch laminate. Other conventional methods for stretch laminate formation are within the scope of this description.

Figure 1E:
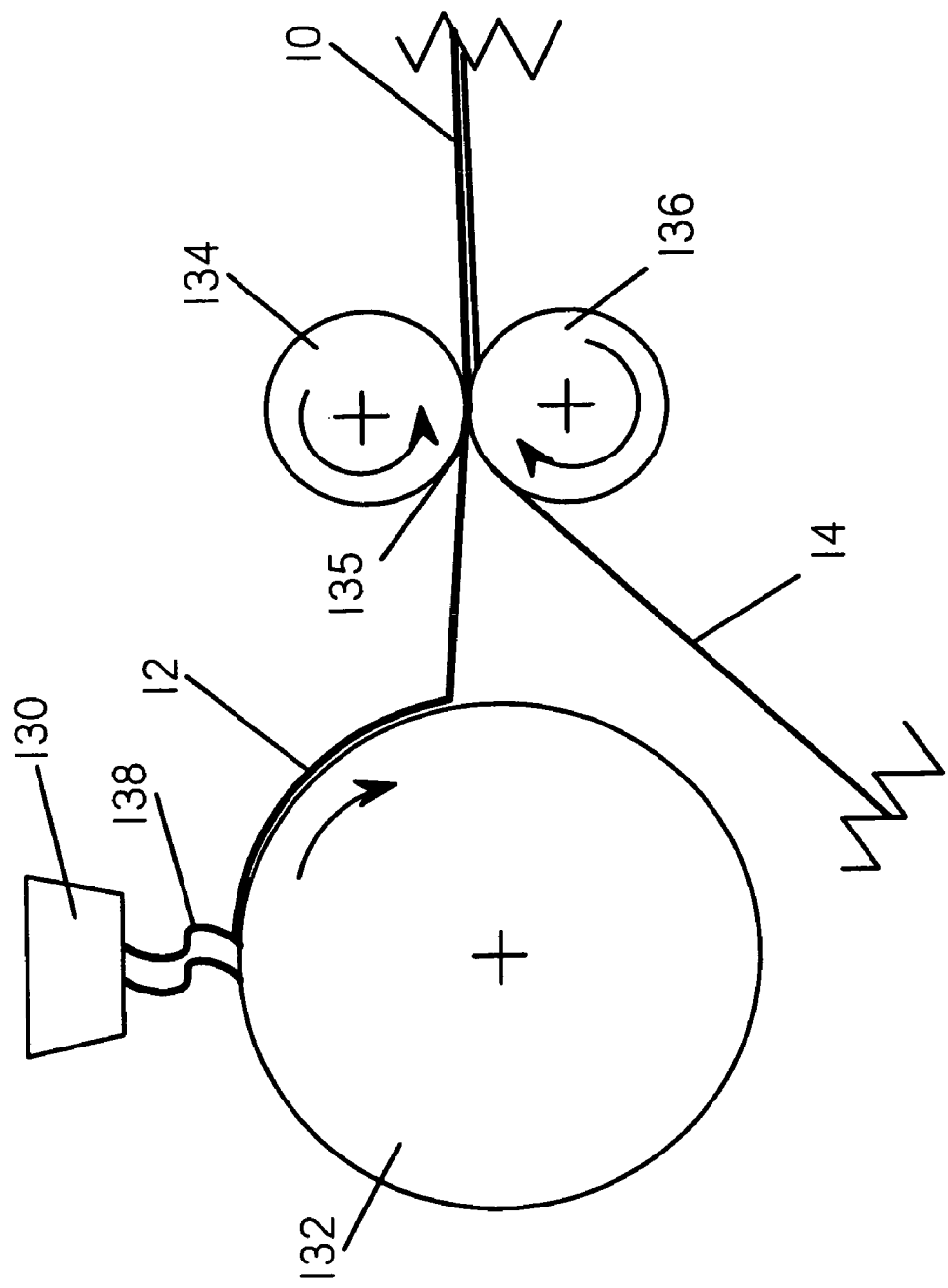
FIG. 1E is a schematic of a suitable process for forming the breathable stretch laminate.

In an alternate embodiment, the breathable stretch laminate 10 may be formed by an integrated process. The process may involve the elastic member 12 being formed contemporaneously with the formation of the laminate 10. In other words, the elastic member 12 may be formed as one step in the uninterrupted process of making the laminate 10. In one suitable process as shown in FIG. 1E, a cooling drum 132 is provided. The cooling drum 132 rotates about an axis and may have a cooled outer surface. An extruder 130 is provided that extrudes a molten or softened elastomeric composition 138 onto the cooled outer surface of the cooling drum to form one or more elastic members 12. A first roller 134 and a second roller 136 rotating about parallel axes may be provided. The first and second rollers 134, 136 may form a nip 135 there between. The substrate 14 may be provided and may be conveyed to the second roller 136. The elastic members 12 may be conveyed from the cooling drum 132 to the first roller 134. Generally, the distance between the cooling drum 132 and the first roller 134 should be minimized to improve the handling efficiency of the elastic members 12. The elastic members 12 and substrate 14 are passed through the nip 135 thereby joining the plurality of elastic members 12 to the substrate 14. An adhesive may be used to improve the attachment between the elastic members 12 and the substrate 14. Additional substrates may be joined to the breathable stretch laminate 10. The resulting laminate may be subjected to further processing such as incremental stretching by way of corrugated rolls.

Furthermore, the surface speed of the first roller 134 may be greater than the surface speed of the cooling drum 132. In such a case, the elastic members 12 may be elongated prior to attachment to the substrate 14.

C. Elastic Member

The elastic member 12 may comprise a polyurethane, optionally at least one modifying resin, and optionally one or more additives. As used herein, polyurethane includes polymers having a urethane and/or urea linkage. The polyurethanes useful herein are preferably selected from: polyurethane (co)polyethers, polyurethane (co)polyesters, polyurethane/urea (co)polyethers, or polyurethane/urea (co)polyesters, Preferred are polyurethane-co-poly(ethylene glycol), polyurethane-co-poly(tetramethylene glycol), and polyurethane-co-poly(propylene glycol) and mixtures thereof.

The basis weight of the elastic member 12 may be varied. In certain embodiments, the elastic member 12 may have a basis weight of less than about 100 g/m$^2$ (e.g., use of the BSL 10 in the front or back ear of a pant as discussed below in reference to FIGS. 3A-B). In certain embodiments, the elastic member 12 may have a basis weight of less than about 35 g/m$^2$ (e.g., use of the BSL 10 in the front or back ear of a diaper as discussed below in reference to FIG. 2). In certain embodiments, the elastic member 12 may have a basis weight of less than about 10 g/m$^2$ (e.g., use of the BSL 10 in an elastic backsheet).

The polyurethanes may be component of a phase separating material having at least one hard phase (also referred to as a hard block or hard segment) and at least one soft phase (also referred to as a soft block or soft segment). Each phase may exhibit a distinct glass transition temperatures. The soft phase generally exhibits a sufficiently low glass transition (Tg) temperature and/or melting temperature so as not to form glassy or crystalline regions at the use temperature of the copolymer. In one embodiment, the use temperature may be between about room temperature (about 22° C.) and about body temperature (about 37° C.). However, other use temperatures are envisioned and within the scope of this invention. Such soft phases may exhibit a Tg of less than about −40° C. The soft phase may exhibit a Tg of less than about −65° C. or about −75° C. The hard phase may have a Tg greater than about 65° C. The hard phase may exhibit a Tg of greater than about 135° C.

Glass transition temperatures referred to herein are determined by Differential Scanning Calorimetry (DCS) using a temperature ramp rate of 20° C./min. The calorimeter should be capable of heating/cooling rates of at least 20° C./min over a temperature range, which includes the expected Tg's of the sample that is to be tested, e.g. of from −90° to 250° C., and the calorimeter should have a sensitivity of about 0.2 μW. The Q1000 DSC available from TA Instruments of New Castle, Del. is well-suited to determining the Tg's referred to herein. The material of interest can be analyzed using a temperature program such as: equilibrate at −90° C., ramp at 20° C./min to 120° C., hold isothermal for 5 minutes, ramp 20° C./min to −90° C., hold isothermal for 5 minutes, ramp 20° C./min to 250° C. The data (heat flow versus temperature) from the second heat cycle is used to calculate the Tg via a standard half extrapolated heat capacity temperature algorithm. Typically, 3-5 g of a sample material is weighed (±0.1 g) into an aluminum DSC pan with crimped lid.

The hard phase may comprise a polyurethane block meeting the requisite glass transition temperature requirements. The soft phase may comprise one or more polyethers. Suitable polyethers include polyethylene glycol, polytetramethylene glycol, polypropylene glycol, and mixture thereof. Polyethylene glycol soft blocks are useful since polyurethanes block copolymers with polyethylene glycol blocks are more breathable than those containing polytetramethylene glycol or polypropylene glycol. Although polyethylene glycol blocks provide ideal breathability, a mixture of polyethylene glycol blocks with other polyethers (e.g., polytetramethylene glycol) blocks is particularly suited to give mechanical properties suitable for use in stretch laminates. The soft phase polyethers may be provided by polymerization of the hard phase component with a macrodiol. Macrodiols may have a base structure of HO—(—R—O—)$_n$—H where R is a repeat unit such as ethylene, butane, hexane, etc. and where n is greater than 1. By way of example, suitable macrodiols include polymers of ethylene glycol, butane diol, hexane diol, dipropylene diol, cyclohexylenediol, and combinations. Furthermore, the soft phase may be provided by polymerization of the hard phase component with suitable hydroquinoines including ethoxylated hydroquinone. The phase separating material optionally may be grafted and/or be partially modified with chemical substituents (e.g., hydroxyl groups or carboxylates) to tailor the Tg of the soft block, to affect surface characteristics, or to increase breathability.

In certain embodiments, polyurethane may have a weight average molecular weight of at least 40 kDa. In certain embodiments, the molecular weight of the soft phase may be at least 500 Da, at least 1000 Da, or even at least 2000 Da.

The polyurethane may be derived from a polymerisation reaction of a diisocyanate with a diol, such as, for example, butane diol, or cyclohexane diol. Alternately, the polyurethane may be derived from a polymerisation reaction of an aromatic diisocyanate and an aliphatic diol such as ethylene glycol, butane diol, propane diol, or mixtures thereof. A suitable diisocyanate used to form the polyurethane or the polyurethane segments of the block copolymer is methylene bis (phenyl isocyanate).

The polyurethane may contain a polyether intermediate derived from tetrahydrofuran monomers so that tetramethylene oxide repeat units are present in the intermediate which also has terminal hydroxyl groups. Optionally, selective types of other alkylene oxide monomers such as propylene oxide, ethylene oxide or a mixture of propylene oxide with ethylene oxide can be utilized to produce the polyurethane.

A suitable phase separating material may be polymerized from the starting monomers of (i) a polyether intermediate having at least a tetramethylene oxide repeat unit and, optionally, a repeat unit derived from propylene oxide and/or ethylene oxide; (ii) a diisocyannate; and (iii) a diol or ethoxylated hydroquinone. Suitable diols include ethylene glycol, butane diol, hexane diol, dipropylene diol, cycolhexylenediol, and combinations.

The elastic member 12 may comprise one or more plasticizers. Suitable plasticizers may associate or phase mix elastomeric polymer to reduce hardness without effecting properties. The elastic member 12 may comprise plasticizers in amounts from about 0% to about 60%. Suitable plasticizers include benzyl phthalate, benzyl butyl phthalate, and poly (ethylene glycol) such as PEG-400.

The elastic member 12 may comprise a variety of additives. Suitable additives include, for example, stabilizers, anti-blocking agents, viscosity modifiers, processing aids, slip agents antioxidants, opacifying pigments, colorants, mineral fillers, UV absorbers and bacteriostats may be employed to prevent thermal, oxidative, and bio-chemical degradation of the elastic member 12. Generally, additives may account for about 0.01% to about 60% of the total weight of the elastic member 12. In other embodiments, the composition comprises from about 0.01% to about 25%. In other suitable embodiments, the composition comprises from about 0.01% to about 10% by weight, of additives.

Various colorants and fillers are known in the art and may be included as additives within the composition that forms the elastic member 12. Colorants can include dyes and pigments such as titanium dioxide. Fillers may include such materials as talc and clay. Other additives may include dyes, UV absorbers, odor control agents, perfumes, fillers, desiccants, and the like.

D. Substrates

Suitable substrates 14 for use include nonwoven webs, woven webs, knitted fabrics, films, film laminates, apertured films, nonwoven laminates, sponges, foams, scrims, and any combinations thereof. Suitable substrates may comprise natural materials, synthetic materials, or any combination thereof. For use in absorbent articles and particularly in diapers and like products, the substrate 14 is generally compliant, soft-feeling, and non-irritating to a wearer's skin. In certain embodiments, substrates 14 may include nonwoven webs such as spunbond webs, meltblown webs, carded webs, and combinations thereof (e.g., spunbond-meltblown composites and variants).

E. Characteristics of the Breathable Stretch Laminate

The BSL 10 of the present invention exhibits unique physical characteristics. In certain embodiments, it is important for the BSL 10 to exhibit a requisite degree of breathability as determined by the Moisture Vapor Transmission Rate (MVTR) test described below. The BSL 10 may exhibit a MVTR of at least about 300 g/m$^2$/24 hours. In alternate embodiments, the BSL 10 may exhibit a MVTR of at least about 500, 750, or 1000 g/m$^2$/24 hours.

The BSL 10 may exhibit a force relaxation of less than about 50% as determined by the Sustained Force Relaxation Test described below. In alternate embodiments, the BSL 10 may exhibit a force relaxation of less than about 40%, 30%, or 25%. Furthermore, the BSL 10 may exhibit a 200% load to 50% unload ratio, as measured in the first cycle according to the 200% 2 Cycle Hysteresis Method described below, of less than about 16. In other embodiments, the 200% load to 50% unload ratio is less than about 13. A smaller value for the load-to-unload ratio correlates to a smaller hysteresis area under the curve which evidences the presence of higher unload forces at lower strains (i.e., the unload forces more closely approximate the load forces).

III. Absorbent Article

The BSL 10 may be utilized in a variety of consumer and commercial products. However, the BSL 10 has particular benefit within absorbent articles, particularly disposable absorbent articles such as diapers and the like. The BSL 10 may be used in a variety of regions or in a variety of elements to provide elastic character to the absorbent article.

Figure 2:
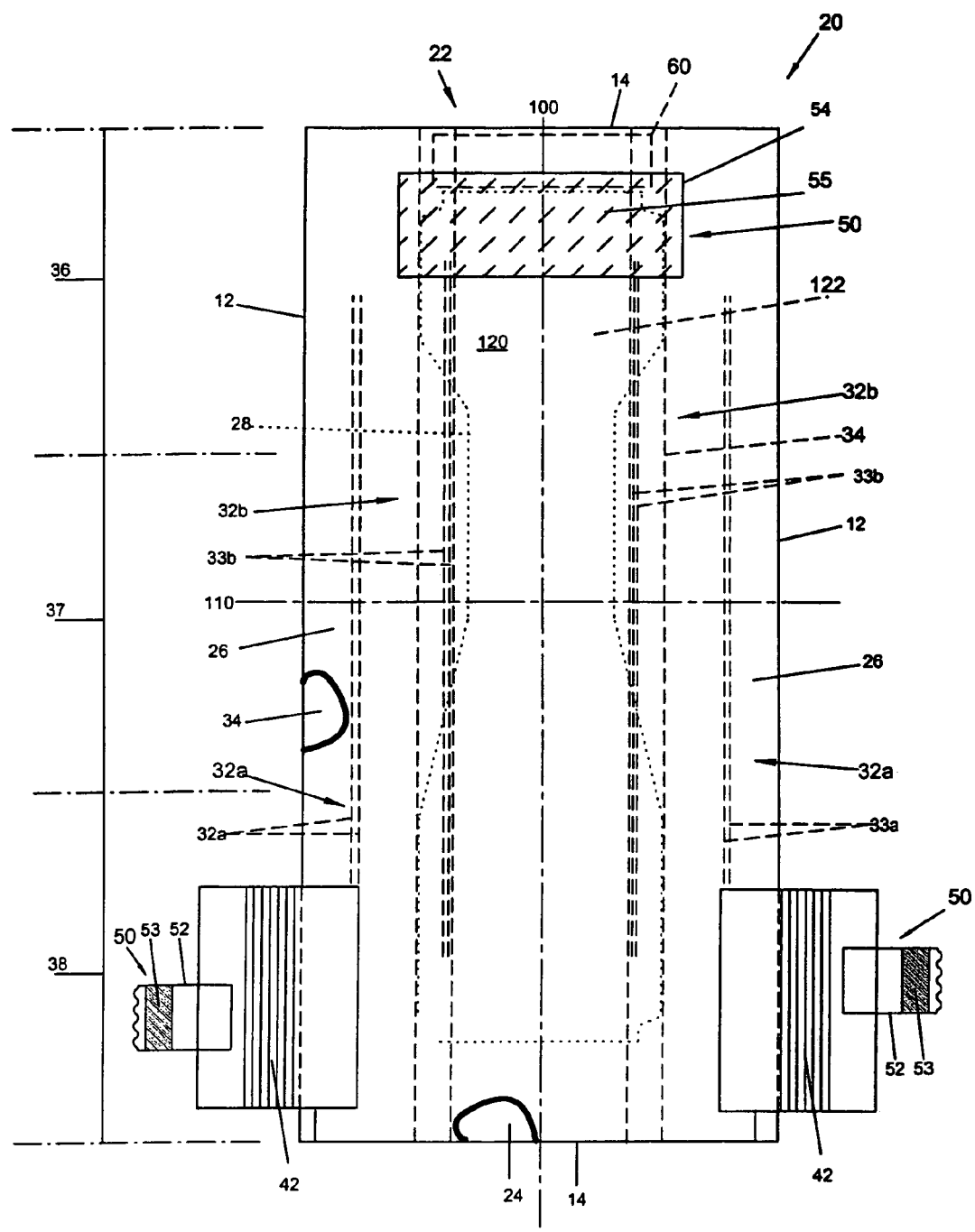
FIG. 2 is a top plan view of a diaper containing the breathable stretch laminate.

FIG. 2 is a plan view of an exemplary, non-limiting embodiment of a diaper 20 in a flat, uncontracted state (i.e., without elastic induced contraction). The garment-facing surface 120 of the diaper 20 is facing the viewer and the body-facing surface 122 is opposite the viewer. The diaper 20 includes a longitudinal centerline 100 and a lateral centerline 110. The diaper 20 may comprise a chassis 22. In certain embodiments, the chassis 22 comprises the main structure of the diaper 20 and other features may be added to form the composite diaper structure. The diaper 20 and chassis 22 are shown to have a front waist region 36, a back waist region 38 opposed to the front waist region 36, and a crotch region 37 located between the front waist region 36 and the back waist region 38. The waist regions 36 and 38 generally comprise those portions of the diaper 20 which, when worn, encircle the waist of the wearer. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer.

The outer periphery of diaper 20 and/or chassis 22 is defined by longitudinal edges 12 and lateral edges 14. The chassis 22 may have opposing longitudinal edges 12 that are oriented generally parallel to the longitudinal centerline 100. However, for better fit, longitudinal edges 12 may be curved or angled to produce, for example, an "hourglass" shape diaper when viewed in a plan view. The chassis 22 may have opposing lateral edges 14 that are oriented generally parallel to the lateral centerline 110.

The chassis 22 may comprises a topsheet 24 having longitudinal edges 25, a backsheet 26, and an absorbent core 28 between the topsheet 24 and the backsheet 26. The absorbent core 28 may have a body-facing surface and a garment facing-surface. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. The topsheet 24, the backsheet 26, and the absorbent core 28 may be assembled in a variety of well-known configurations as described generally in U.S. Pat. Nos. 3,860,003; 5,151,092; 5,221,274; 5,554,145; 5,569,234; 5,580,411; and 6,004,306.

The absorbent core 28 may comprise a wide variety of other liquid-absorbent materials commonly used in disposable diapers and other absorbent articles. Examples of suitable absorbent materials include comminuted wood pulp, which is generally referred to as air felt; chemically stiffened, modified or cross-linked cellulosic fibers; superabsorbent polymers or absorbent gelling materials; melt blown polymers, including co-form, biosoluble vitreous microfibers; tissue, including tissue wraps and tissue laminates; absorbent foams; absorbent sponges; and any other known absorbent material or combinations of materials. Exemplary absorbent structures for use as the absorbent core 28 are described in U.S. Pat. No. 4,610,678; 4,673,402; 4,834,735; 4,888,231; 5,137,537; 5,147,345; 5,342,338; 5,260,345; 5,387,207; 5,397,316; 5,625,222; and 6,932,800. Further exemplary absorbent structures may include non-removable absorbent core components and removable absorbent core components. Such structures are described in U.S. Publication 2004/0039361A1; 2004/0024379A1; 2004/0030314A1; 2003/0199844A1; and 2005/0228356A1.

The absorbent core 28 may comprise a fluid acquisition component, a fluid distribution component, and a fluid storage component. A suitable absorbent core 28 comprising an acquisition layer, a distribution layer, and a storage layer is described in U.S. Pat. No. 6,590,136.

Another suitable absorbent core construction is described in U.S. Publication No. 2004/0167486 to Busam et al. The absorbent core of the aforementioned publication uses no or, in the alternative, minimal amounts of absorbent fibrous material within the core. Generally, the absorbent core may include no more than about 20% weight percent of absorbent fibrous material (i.e., [weight of fibrous material/total weight of the absorbent core]×100).

The topsheet 24 is generally a portion of the diaper 20 that may be positioned at least in partial contact or close proximity to a wearer. Suitable topsheets 24 may be manufactured from a wide range of materials such as woven or nonwoven webs of natural fibers (e.g., wood or cotton fibers), synthetic fibers (e.g., polyester or polypropylene fibers), or a combination of natural and synthetic fibers; apertured plastic films; porous foams or reticulated foams. The topsheet 24 is generally supple, soft feeling, and non-irritating to a wearer's skin. Generally, at least a portion of the topsheet 24 is liquid pervious, permitting liquid to readily penetrate through the thickness of the topsheet 24. Suitably, the topsheet 24 comprises a polymer (e.g. polyethylene) derived from a renewable resource. Alternatively, a suitable topsheet 24 is available from BBA Fiberweb, Brentwood, Tenn. as supplier code 055SLPV09U. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

Any portion of the topsheet 24 may be coated with a lotion as is known in the art. Examples of suitable lotions include those described in U.S. Pat. Nos. 5,607,760; 5,609,587; 5,635,191; and 5,643,588. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

The backsheet 26 is generally positioned such that it may be at least a portion of the garment-facing surface 120 of the diaper 20. Backsheet 26 may be designed to prevent the exudates absorbed by and contained within the diaper 20 from soiling articles that may contact the diaper 20, such as bed sheets and undergarments. In certain embodiments, the backsheet 26 is substantially water-impermeable; however, the backsheet 26 may be made breathable so as to permit vapors to escape while preventing liquid exudates from escaping. The polyethylene film may be made breathable by inclusion of inorganic particulate material and subsequent tensioning of the film. Breathable backsheets may include materials such as woven webs, nonwoven webs, composite materials such as film-coated nonwoven webs, and microporous films. Suitably, the backsheet 26 comprises a polymer such (e.g. polyethylene) derived from a renewable resource as disclosed above. Alternative backsheets 26 derived from non-renewable resources include films manufactured by Tredegar Industries Inc. of Terre Haute, Ind. and sold under the trade names X15306, X10962, and X10964; and microporous films such as manufactured by Mitsui Toatsu Co., of Japan under the designation ESPOIR NO and by EXXON Chemical Co., of Bay City, Tex., under the designation EXXAIRE. Other alternative breathable backsheets 26 are described in U.S. Pat. Nos. 5,865,823, 5,571,096, and 6,107,537.

Backsheet 26 may also consist of more than one layer. For example, the backsheet 26 may comprise an outer cover and an inner layer. The outer cover may have longitudinal edges and the inner layer may have longitudinal edges. The outer cover may be made of a soft, non-woven material. The inner layer may be made of a substantially water-impermeable film. The outer cover and an inner layer may be joined together by adhesive or any other suitable material or method. Suitably, the nonwoven outer cover and the water-impermeable film comprise polymers (e.g., polyethylene) derived from. renewable resources. Alternatively, a suitable outer cover and inner layer derived from non-renewable resources are available, respectively, as supplier code A18AH0 from Corovin GmbH, Peine, Germany and as supplier code PGBR4WPR from RKW Gronau GmbH, Gronau, Germany. While a variety of backsheet configurations are contemplated herein, it would be obvious to those skilled in the art that various other changes and modifications can be made without departing from the spirit and scope of the invention.

The breathable stretch laminate 10 of the present invention may be joined to the backsheet 26, topsheet 24, or absorbent core 28 or formed from one or more components that form the backsheet 26, topsheet 24, or absorbent core 28. Furthermore, the backsheet 26, topsheet 24, or absorbent core 28 may comprise the breathable stretch laminate 10. For example, the backsheet 26 may comprise the breathable stretch laminate 10 thereby forming an elastic backsheet 26. The breathable stretch laminate 10 may be disposed in any location where elastic character is desired.

The diaper 20 may include back ears 42 (shown in FIG. 2), front ears 40, or both (shown in FIG. 3). The front and/or back ears 42 may be unitary elements of the diaper 20 (i.e., they are not separately manipulative elements secured to the diaper 20, but rather are formed from and are extensions of one or more of the various layers of the diaper). In certain embodiments, the ears 40, 42 may be discrete elements that are joined to the chassis 22, as shown in FIG. 2. Discrete ears 40, 42 may be joined to the chassis 22 by any bonding method known in the art such as adhesive bonding, pressure bonding, heat bonding, and the like. In other embodiments, the ears 40, 42 may comprise a discrete element joined to the chassis 22 with the chassis 22 having a layer, element, or substrate that extends over the ear 40, 42. The ears 40, 42 may be extensible, inextensible, elastic, or inelastic. The ears 40, 42 may be formed from nonwoven webs, woven webs, knitted fabrics, polymeric and elastomeric films, apertured films, sponges, foams, scrims, and combinations and laminates thereof. In certain embodiments the front ears and back ears 42 may be formed of the breathable stretch laminate 10 of the present invention.

The diaper 20 may further include leg cuffs 32*a*, 32*b* which provide improved containment of liquids and other body exudates. Leg cuffs 32*a*, 32*b* may also be referred to as gasketing cuffs, outer leg cuffs, leg bands, side flaps, elastic cuffs, barrier cuffs, second cuffs, inner leg cuffs, or "stand-up" elasticized flaps. U.S. Pat. No. 3,860,003 describes a disposable diaper which provides a contractible leg opening having a side flap and one or more elastic members to provide an elasticized leg cuff (i.e., a gasketing cuff). U.S. Pat. Nos. 4,808,178 and 4,909,803 describe disposable diapers having "stand-up" elasticized flaps (i.e., barrier cuffs) which improve the containment of the leg regions. U.S. Pat. Nos. 4,695,278 and 4,795,454 describe disposable diapers having dual cuffs, including gasketing cuffs and barrier cuffs.

FIG. 2 shows the diaper 20 having dual cuffs, gasketing cuff 32*a* and barrier cuff 32*b*. The barrier cuff 32*b* may include one or more barrier elastic members 33*b*. The barrier elastic members 33*b* may be joined to a barrier cuff substrate 34. In certain embodiments, the barrier cuff substrate 34 may be a polymeric film or nonwoven. The barrier cuff 32*b* may be disposed on the body-facing surface of the chassis 22. The barrier cuff 32*b* may comprise the breathable stretch laminate 10 of the present invention wherein the elastic member 12 and substrate 14 of the BSL 10 correspond to the barrier elastic members 33*b* and barrier cuff substrate 34 of the barrier cuff 32*b*. The barrier cuff substrate 34 may extend laterally from the longitudinal edge 12 of the chassis 22 to a point inboard of the longitudinal edge 122. The barrier cuff 32*b* generally extends longitudinally at least through the crotch region 37.

The gasketing cuff 32*a* may include one or more gasketing elastic members 33*a*. The gasketing elastic member 33*a* may be joined to one or more of the existing elements or substrates of the diaper 20 (e.g., topsheet 24, backsheet 26, barrier cuff substrate 34, etc.). The gasketing cuff 32*a* may comprise the breathable stretch laminate 10 of the present invention wherein the elastic member 12 and substrate 14 of the BSL 10 correspond to the gasketing elastic members 33*a* and any one or more of the existing elements or substrates of the diaper 20.

The diaper 20 may also comprise an elastic waist feature 60. The elastic waist feature 60 is generally intended to elastically expand and contract to dynamically fit the wearer's waist. The waist feature 60 may enable the diaper 20 to provide improved fit and containment. The diaper may have two elastic waist features 60, one disposed in the front waist region 36 and one disposed in the back waist region 38. The elastic waist feature 60 may be a discrete element joined to the diaper 20 or the elastic waist feature 60 may be integral to the diaper 60 (i.e., the elastic waist feature 60 is not a separate element but is a region of the diaper 20 exhibiting elasticity). The waist elastic 62 generally will allow for lateral elongation and recovery. In other embodiment, the elastic waist feature 60 may comprise the breathable stretch laminate 10 of the present invention.

The diaper 20 may also include a fastening system 50. When fastened, the fastening system 50 interconnects the front waist region 36 and the back waist region 38 resulting in a waist circumference that may encircle the wearer during wear of the diaper 20. The fastening system 50 may include an engaging member 52 and a receiving member 54. The engaging member 52 may have an engaging surface 53 that covers a portion or the entire engaging member 52. The engaging surface 53 may comprise hooks, loops, an adhesive, a cohesive, a button, or other fastening element. The receiving member 54 may comprise a receiving surface 55 accepts engagement of the engaging member 52. The receiving surface 55 may cover a portion of the entire receiving member 54. The receiving surface 55 is constructed to mate with or engage with the engaging surface 53 of the engaging member 52. For example, a receiving surface 55 of looped or nonwoven may be paired with an engaging surface 53 of hooks. The fastening system 50 may comprises a fastener such as tape tabs, hook and loop fastening components, interlocking fasteners such as tabs & slots, buckles, buttons, snaps, and/or fastening components, although any other known fastening means are generally acceptable.

Exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 50 may also provide a means for holding the article in a disposal configuration as disclosed in U.S. Pat. No. 4,963,140. The fastening system 50 may also include primary and secondary fastening systems, as disclosed in U.S. Pat. No. 4,699,622. The fastening system 50 may be constructed to reduce shifting of overlapped portions or to improve fit as disclosed in U.S. Pat. Nos. 5,242,436; 5,499,978; 5,507,736; and 5,591,152.

In alternative embodiments, the diaper may be pre-formed by the manufacturer to create a pant. The pant may be pre-formed such that the first waist region 36 is joined to the back waist region 38 thereby forming a waist opening back waist region 38 by a refastenable mechanism such as fastening system or may be joined by a refastenable and/or a non-refastenable bond (e.g., seam, weld, adhesive, cohesive bond, fastener, etc.). A suitable refastenable bond may be provided with the use of a fastening system 50. A non-refastenable bond may be formed by common bonding techniques including adhesive bonding, a pressure bonding, a heat bonding, ultrasonic bonding, and the like.

Figure 3A:
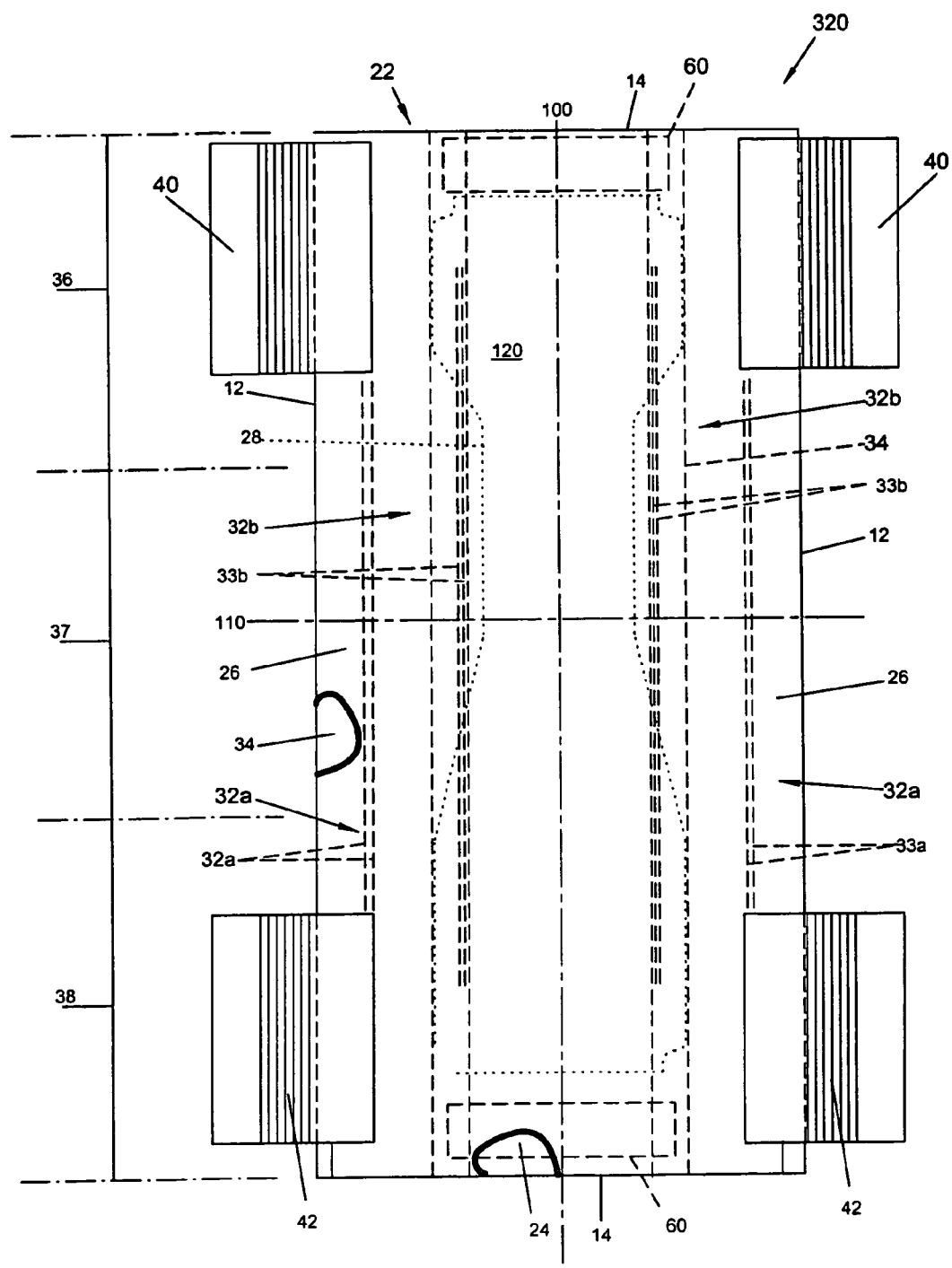
FIG. 3A is a top plan view of a pant containing the breathable stretch laminate.
Figure 3B:
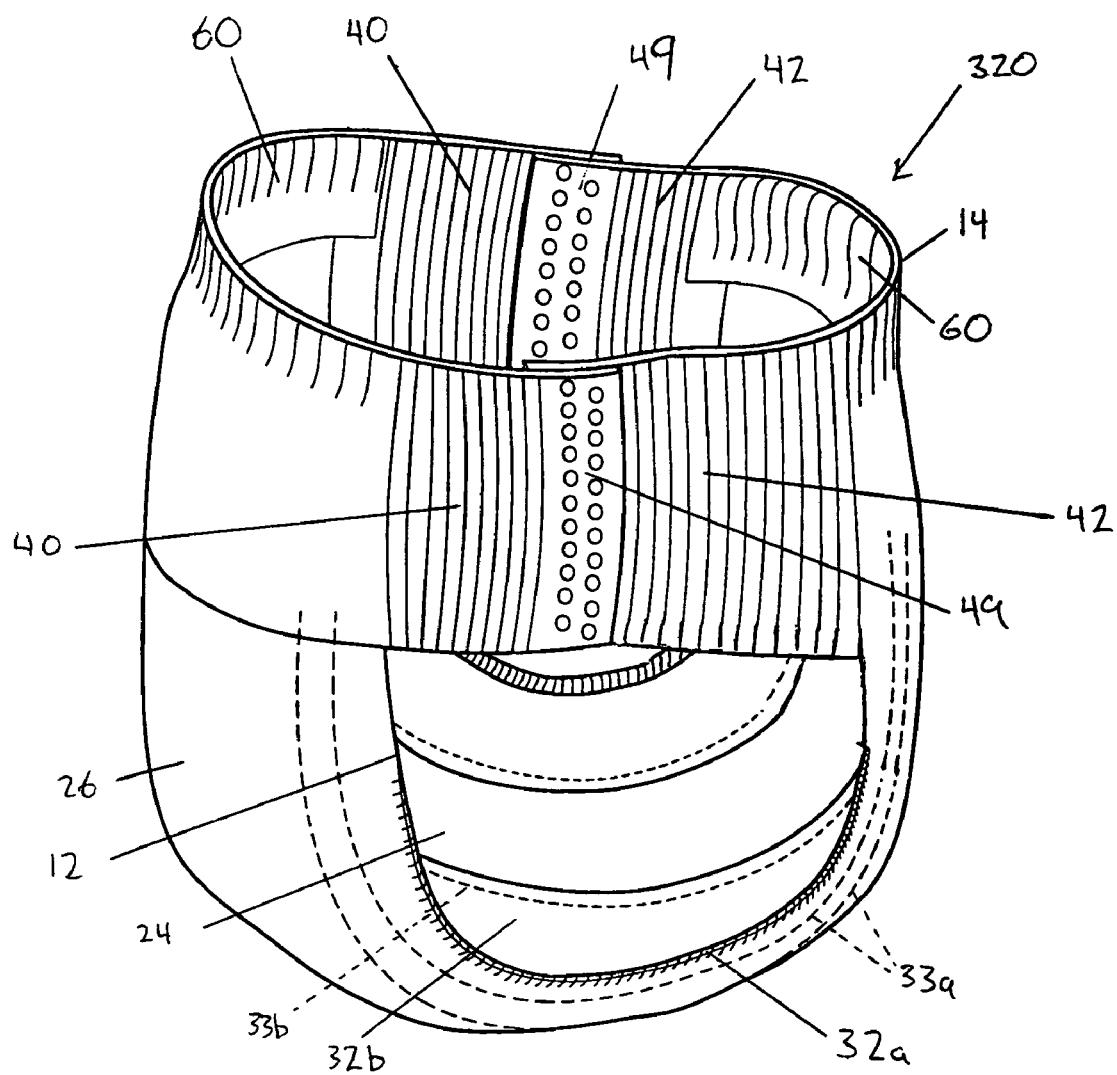
FIG. 3B is a perspective view of the pant, as shown in FIG. 3A, containing the breathable stretch laminate.

An exemplary pant 320 is shown in FIGS. 3A-B. FIG. 3A shows the pant 320 in a planar unseamed state with the garment-facing surface 120 facing the viewer. FIG. 3B shows the pant 320 of FIG. 3A in a seamed state and from a perspective view. Unless noted otherwise, the callouts of in FIGS. 3A-B refer to the same elements as the diaper 20 of FIG. 2. The pant 320 shown without a fastening system. The front ear 40 and back ear 42 are joined at a seam 49 by multiple bonds. The pant 320 is also shown having a waist feature 60 in both the front waist region 36 and the back waist region 38. Other suitable pants are disclosed in U.S. Pat. Nos. 5,246,433; 5,569,234; 6,120,487; 6,120,489; 4,940,464; 5,092,861; 5,897,545; 5,957,908; and U.S. patent application Ser. No. 10/171,249.

TEST METHODS

Sustained Load Force Relaxation

Sample laminates are cut using a 1"×2" die. The weight and the thickness of the laminates are recorded as well as the process direction (MD or CD). Polyester backed high temperature tape (available from McMaster-Carr Catalogue item #7630A42) is applied to the top and bottom 0.5 inches of the cut laminate, leaving a 1 inch gage length. The sample is placed into vertically aligned GF-1 Vise Action Tensile Grips available from Chatillon Force Measurement Systems, Largo, Fla., which are within a test chamber (described below) set at 100° F. Once the temperature has equilibrated to 100° F., the data acquisition software is engaged and the sample is manually strained to 50% engineering strain (1.5 inch grip separation). Force (N) is recorded for 10 hours (the sampling rate is decreased as time progresses during the test to minimize the data file size). The force relaxation at a given time, t, is calculated according to [(initial force-force at time t)/initial force].

Sustained Load Force Relaxation Test Chamber: The test chamber consists of a 25×11×16 inch (height×width×depth) enclosure surrounding a tubular stand which supports a pair of vertically aligned manually actuated grips. The top grip is fixed to a force transducer, Interface Model SMT1-1.1 available from Interface, Inc., Scottsdale, Ariz. The bottom grip is attached to a manually actuated screw which allows for the grip to raised and lowered. The zero position for the grips provides for a 1.0 inch gap between said grips. An electronic positioning device, ProScale Model 150 available from Accurate Technology, Inc., of Fletcher, N.C., is attached to the bottom grip to monitor the distance between the grips. The temperature within the test chamber is maintained using an electronic controller (West 6100+, available from ISE, Inc., Cleveland, Ohio), resistance heater, and thermocouple positioned near the test sample. The output signal from the force transducer is processed using Interface Model SGA Strain Gage Transducer Amplifier available from Interface, Inc. Scottsdale, Ariz. and captured on a Dell Latitude (available from Dell Inc., Round Rock, Tex.) computer using Measurement Computing Corporation (Middleboro, Mass.) PC card DAS16/16. The data acquisition software, developed in-house, logs time and load at programmed time intervals.

200% 2 Cycle Hysteresis Method

A uniaxial strain is applied to a flat sample and measuring the force that is required to elongate the sample. The film samples are herein strained in the cross-direction, when applicable. Sample laminates are cut using a 25×50 mm (width× length) die. The 25×50 mm sample is placed into the pneumatic grips of a MTS Synergie 200 materials tester available from MTS Corporation, Cary, N.C., with a 1.0 inch grip separation between (zero position) the grips which are available as Advantage Pneumatic Grips Model 200N from MTS Corporation, Cary, N.C. The grips are vertically aligned with the bottom grip fixed to the frame and the top grip attached to the force transducer, MTS model #100-090-197 available from MTS Corporation, Cary, N.C., which is attached to the machine crosshead. The full scale capacity of the load cell must exceed the greatest resistance load from the test film during the test. The test consists of two move segments. The first move segment consists of the crosshead extending the film to 200% engineering strain (3 inch grip separation) at 250 mm/minute and holding the sample at 200% strain for 30 seconds and then returning the crosshead to the zero position at 250 mm/min. The sample is held at the zero position for 60 seconds. The second move segment is a repetition of the first. The first move segment is identified as cycle 1, while the second move segment is identified as cycle 2. The method reports Load at 200% (peak load at 200% engineering strain), Unload at 50% (load at 50% engineering strain during return movement to zero), and Unload at 30% (load at 50% engineering strain during return movement to zero).

Moisture Vapor Transmission Rate (MVTR) Method

The MVTR method measures the amount of water vapor that is transmitted through a sample under specific temperature and humidity. The transmitted vapor is absorbed by $CaCl_2$ desiccant and determined gravimetrically. Samples are evaluated in triplicate, along with a reference film sample of established permeability (e.g., Exxon Exxaire microporous material #XBF-110W) that is used as a positive control.

The test uses a flanged cup (machined from Delrin (McMaster-Carr Catalog #8572K34) and anhydrous $CaCl_2$ (Wako Pure Chemical Industries, Richmond, Va.; Catalog #030-00525). The height of the cup is 55 mm with an inner diameter of 30 mm and an outer diameter of 45 mm. The inner volume of the cup is approximately 38.8 $cm^3$. The cup is fitted with a silicone gasket and lid containing 3 holes for thumb screws to completely seal the cup. Desiccant particles used are sized to pass through a No. 8 sieve but not through a No. 10 sieve. Samples are resized to approximately 1.5"×2.5" and are substantially free of visible defects such as air bubbles, holes, inclusions, and cuts. Samples are to have sharp and visibly defect-free edges. If the sample is defective, it is to be discarded and replaced. The sample must completely cover the cup opening having a circular area 0.0007065 $m^2$.

The cup is filled with $CaCl_2$ to within about 1 cm of the top. The cup is tapped on the counter 10 times, and the $CaCl_2$ surface is leveled. The amount of $CaCl_2$ is adjusted until the headspace between the film surface and the top of the $CaCl_2$ is 1.0 cm. The film is placed on top of the cup across the opening (30 mm) and is secured using the silicone gasket, retaining ring, and thumb screws. Properly installed, the specimen should not be wrinkled or stretched. The sample assembly is weighed with an analytical balance and recorded to ±0.001 g. The assembly is placed in a constant temperature (40±3° C.) and humidity (75±3% RH) chamber for 5.0 hr±5 min. The sample assembly is removed, covered with Saran Wrap® and is secured with a rubber band. The sample is equilibrated to room temperature for 30 min, the plastic wrap and rubber band are removed, and the assembly is reweighed and the weight is recorded to ±0.001 g. The absorbed moisture $M_a$ is the difference in initial and final assembly weights. MVTR, in $g/m^2/24$ hr ($g/m^2$/day), is calculated as:

$$MVTR = M_a/(A*0.208 \text{ day})$$

Replicate results are averaged and rounded to the nearest 100 $g/m^2/24$ hr (e.g., 2865 $g/m^2/24$ hr is herein given as 2900 $g/m^2/24$ hr and 275 $g/m^2/24$ hr is given as 300 $g/m^2/24$ hr).

SAMPLE PREPARTION

Preparation of Laminates

Glue sheets are prepared ahead of time on an X-Y table (i.e., a table equipped with a mechanical glue head that can travel in both the x and y directions) by applying adhesive code H2861 available from Bostik Findley, Wauatosa, Wis., using a single nozzle head in a spiral pattern with a 5 mm overlap on Silicon coated release paper. Pre-determined cut pieces of a 27 gsm High Elongation Carded nonwoven (NW) available from BBA Nonwovens, Old Hickory, Tenn., are cut for laminate making. Two pieces of nonwovens are secured properly to a rubber mat by tape while glue sheets are placed on top of secured nonwovens. While the other side of glue sheets are still covered with release paper, a roller is used to press/transfer adhesive from the release papers to the nonwoven. The release paper is removed from the first nonwoven to expose the adhesive. A predetermined length of elastic film (as disclosed in Examples 1-3 below) is placed on top of first nonwoven/adhesive followed by placing a sheet of release paper on the film. A roller is used to press the film against the first nonwoven/adhesive. The release paper is removed from the film. The release paper on second nonwoven/adhesive is removed. The second nonwoven/adhesive is placed on top of film so the adhesive from the second nonwoven is in contact with film. A roller is used to apply pressure to bond the second nonwoven to the elastomeric film. This process results in production of trilaminate containing adhesively bonded stretch film between two layers of nonwoven. Laminates are cut into a 75 mm (cross machine direction of the film)×80 mm (machine direction of the film) rectangle using a ruler and rolling blade.

Activation of Laminates

Elastic laminates are mechanically activated to simulate ring rolling activation process as described in U.S. Pat. No. 6,843,134. Manual activation in this instance refers to using aluminum plates with inter-meshing teeth to selectively stretch portions of the laminate such that the nonwoven is broken and/or elongated and the elastic film is able to extend and retract without being unduly encumbered by the nonwoven. The laminates are allowed to age for a minimum of 1 day after fabrication and before activation. The laminates are activated with the elongation imparted in the cross direction (CD) with a target strain of 260% and a target strain rate of $533s^{-1}$. The pitch between the activation teeth is approximately 3.810 mm.

EXAMPLES

Example 1

A 34 gsm thermoplastic polyurethane block copolymer cast film available from Deerfield Urethane, Inc., South Deerfield, Mass. as Dureflex X2104 (lot #03162005) was laminated, activated and tested according to the above methods. Dureflex X2104 comprises Estane X-1007 from Noveon, Inc., Cleveland, Ohio. Estante X-1007 is reported as having Tg's of −61° C. and 140° C.

Example 2

A 55 gsm thermoplastic polyurethane block copolymer cast extruded film available from Noveon, Inc., Cleveland, Ohio, as a 90%/10% admix of Estane X-1007-031/X-1206 was laminated, activated, and tested according to the above methods.

Example 3 (Comparative)

A 59 gsm thermoplastic coextruded styrenic block copolymer film available from Nordenia USA, Inc., Jackson, Mo., under supplier code KG6361.000 (lot NOGG53576) was laminated, activated, and tested according to the above methods.

TEST DATA

TABLE 1

Sustained Load Force Relaxation and MVTR Data

| | Force Relaxation % (4 hours) | Force Relaxation % (10 hours) | MVTR (g/m²/24 hours) |
|---|---|---|---|
| Example 1 | 40 | 43 | 1400 |
| Example 2 | 39 | 43 | 1200 |
| Example 3 | 46 | 53 | 300 |

As shown above in Table 1, the force relaxation of the polyurethane based laminates (Examples 1 & 2) are significantly lower than the force relaxation of co-extruded styrenic block copolymer laminates. Additionally, a significant improvement in breathability of these laminates is also demonstrated.

TABLE 2

200% 2-Cycle Hysteresis Data

| Sample ID | Load @ 200% (Cycle 1) (N/cm) | Unload @ 50% (Cycle 1) (N/cm) | Load @ 200% to Unload @ 50% | Load @ 200% (Cycle 2) (N/cm) | Unload @ 50% (Cycle 2) (N/cm) |
|---|---|---|---|---|---|
| Example 1 | 2.63 | 0.17 | 15.5 | 2.19 | 0.16 |
| Example 2 | 3.30 | 0.27 | 12.2 | 2.77 | 0.24 |
| Example 3 | 1.97 | 0.27 | 7.3 | 1.75 | 0.25 |

As exhibited in Table 2, the hysteresis data shows that at comparable basis weights (55 gsm for Example 2 and 59 gsm for Example 3), the unload forces are similar for the polyurethane based laminates and the styrenic block copolymer laminates. However, as the basis weight of the polyurethane film is reduced (e.g., 34 gsm for Example 1), the unload force is likewise diminished compared the styrenic block copolymer laminate. In general, it is desirable to have high unload forces (e.g., unload forces that more closely approximate the load forces). However, it is even more desirable that the force be maintained during strain (i.e., a low force relaxation). In this case, lower unload forces are acceptable since the polyurethane laminates exhibit a reduced force relaxation as compared to the styrenic block copolymer based laminates. As a result, the lower basis weight polyurethane laminate is expected to exhibit unload comparable to the higher basis weight styrenic block copolymer based laminate after 10 hours under strain.

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with a definition or meaning of the term in a document incorporated by reference, the definition or meaning assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a chassis, comprising
      a topsheet;
      a backsheet joined with the topsheet; and
      an absorbent core between the topsheet and backsheet; and
   an ear extending from the chassis, comprising an incrementally stretched, breathable stretch laminate comprising a laminate of:
      first and second nonwoven webs; and
      a monolithic elastic member disposed between and joined to the first and second nonwoven webs, wherein said elastic member comprises a phase-separating material having at least a first phase with a first glass transition temperature of less than −40° C. and a second phase with a second glass transition temperature of greater than 100° C., wherein said second phase comprises a polyurethane;

wherein said breathable stretch laminate exhibits a MVTR greater than about 300 grams per square meter per 24 hours and a force relaxation of less than about 50% after about 10 hours at 100° F. and 50% elongation.

2. The article of claim 1 wherein the breathable stretch laminate exhibits a MVTR greater than about 500 grams per square meter per 24 hours.

3. The article of claim 1 wherein the breathable stretch laminate exhibits a MVTR greater than about 1000 grams per square meter per 24 hours.

4. The article of claim 1 wherein the breathable stretch laminate is a zero strain stretch laminate.

5. The article of claim 1 wherein the breathable stretch laminate in 2 cycle 200% hysteresis test exhibits a first cycle 200% load to 50% unload ratio of less than about 16.

6. The article of claim 1 wherein the polyurethane has a molecular weight of at least 40 kDa.

7. The article of claim 1 wherein the phase-separating material is polymerized from (i) a polyether intermediate having at least a tetramethylene oxide repeat unit and, optionally, a repeat unit derived from propylene oxide and/or ethylene oxide; (ii) a diisocyannate; and (iii) a diol or ethoxylated hydroquinone.

8. An absorbent article comprising:
   a topsheet;
   a backsheet joined with the topsheet;
   an absorbent core between the topsheet and backsheet; and
   an elastic element comprising an incrementally stretched, breathable zero strain stretch laminate comprising
   a nonwoven web; and
   a monolithic elastic member joined to the nonwoven web, wherein said elastic member comprises a phase-separating material having at least a first phase with a first glass transition temperature of less than −40° C. and a second phase with a second glass transition temperature of greater than 100° C., and wherein said second phase comprises a polyurethane;

wherein said breathable zero strain stretch laminate exhibits a MVTR greater than about 300 grams per square meter per 24 hours, a force relaxation of less than about 50% after about 10 hours at 100° F. and 50% elongation, and a first cycle 200% load to 50% unload ratio of less than about 16.

9. An absorbent article comprising:
   a chassis, comprising
      a topsheet;
      a backsheet joined with the topsheet; and
      an absorbent core between the topsheet and backsheet; and
   an ear extending from the chassis, comprising a breathable stretch laminate comprising a laminate of:
      a nonwoven web; and
      a monolithic elastic member joined to the nonwoven web, the elastic member comprising a hard block comprising a polyurethane and a soft block comprising a polyether selected from the group consisting of polyethylene glycol, polypropylene glycol, polytetramethylene glycol, and combinations thereof;

wherein the breathable stretch laminate exhibits a MVTR greater than about 500 grams per square meter per 24 hours and a force relaxation of less than about 50% after about 10 hours at 100° F. and 50% elongation.

10. The article of claim 9 wherein the breathable stretch laminate exhibits a MVTR greater than about 1000 grams per square meter per 24 hours.

11. The article of claim 9 wherein the breathable stretch laminate in 2 cycle 200% hysteresis test exhibits a first cycle 200% load to 50% unload ratio of less than about 16.

* * * * *